(12) United States Patent
Li

(10) Patent No.: US 9,649,491 B2
(45) Date of Patent: May 16, 2017

(54) ELECTRIC STIMULATOR

(71) Applicant: Richard Li, Taichung (TW)

(72) Inventor: Richard Li, Taichung (TW)

( * ) Notice: Subject to any disclaimer, the term of this patent is extended or adjusted under 35 U.S.C. 154(b) by 0 days.

(21) Appl. No.: 14/849,602

(22) Filed: Sep. 10, 2015

(65) Prior Publication Data

US 2017/0072194 A1    Mar. 16, 2017

(51) Int. Cl.
*A61N 1/36* (2006.01)

(52) U.S. Cl.
CPC ............... *A61N 1/36014* (2013.01)

(58) Field of Classification Search
CPC ......... A61N 1/32; A61N 1/326; A61B 5/0492
USPC ....................................... 607/145
See application file for complete search history.

(56) References Cited

U.S. PATENT DOCUMENTS

| 5,620,483 | A | * | 4/1997 | Minogue | ................... | A61N 1/08 |
| | | | | | | 607/115 |
| 6,389,319 | B1 | * | 5/2002 | Lee | .......................... | A61N 1/32 |
| | | | | | | 607/115 |

* cited by examiner

*Primary Examiner* — Christopher D Koharski
*Assistant Examiner* — Roland Dinga
(74) *Attorney, Agent, or Firm* — Leong C. Lei

(57) ABSTRACT

An electric stimulator includes a housing, a control circuit board, and at least two electrode plates. The housing includes an internal space formed therein and an outside surface in which at least one electrode plate retention slot is formed. The control circuit board is mounted in the internal space of the housing to control intensity and frequency of a current output. The electrode plates are electrically conductive and are received in the electrode plate retention slot of the housing and are in electric connection with the control circuit board. The electrode plates have an outside surface including a large-area contact surface and a small-area contact surface connected to the large-area contact surface. The large-area contact surface has a surface area greater than that of the small-area contact surface. The large-area contact surface and the small-area contact surface define therebetween an inclined angle that is not equal to 180 degrees.

8 Claims, 6 Drawing Sheets

ELECTRIC STIMULATOR

TECHNICAL FIELD OF THE INVENTION

The present invention relates generally to physical electric stimulation equipment, and more particularly to an electric stimulator.

DESCRIPTION OF THE PRIOR ART

An electric simulator is a device that generates electric energy signals similar to what generated by a human nervous system and the signal is transmitted to a human body by means of an electrotherapeutic patch that is attached to a surface of the human skin in order to stimulate the nervous system of the human body so that the muscle groups around the electrode may generate a series of localized non-autonomic contraction thereby achieving a desired physical therapeutic effect.

Most of the conventional electric stimulators are connected to the surface of human skin by means of an electrotherapeutic patch. Such an electrotherapeutic patch suffers several drawbacks. For example, there must be electric wires between the electrotherapeutic patch and the equipment and thus, problems that the wires are exposed and may not be easily stowed and may not allow for neat and organized management occur. Further, the electrotherapeutic patch can only be attached to the skin at a site where a sufficient surface area is available and is not fit for small-area portions (such as the periphery of an eye, a corner of a mouth, and a forehead). Further, there is often grease or moisture on the surface of human skin so that the electrotherapeutic patch is readily susceptible to detachment therefrom. In addition, long-term use or repeated attachment may cause the electrotherapeutic patch to lose the adhesion thereof and must be substituted. This causes a waste. Further, the electrotherapeutic patch can provide stimulation to a fixed site only and is not slidable on the skin surface, making it not convenient in use.

SUMMARY OF THE INVENTION

In view of the drawbacks of the conventional electric stimulators that wires are exposed, easy storage may not be possible, neat and organized management may not be allowed, application to small area portions is not possible, detachment may easily occur, adhesion may be lost and waste results, and stimulation can be generated for a fixed site, making the use thereof inconvenient, the present invention aims to provide an electric simulator, which comprises a housing, a control circuit board, and at least two electrode plates. The housing comprises an internal space formed therein and an outside surface in which at least one electrode plate retention slot is formed. The control circuit board is mounted in the internal space of the housing to control intensity and frequency of a current output. The electrode plates are electrically conductive and are received and retained in the electrode plate retention slot of the housing and are in electric connection with the control circuit board. The electrode plates have an outside surface including a large-area contact surface and a small-area contact surface connected to the large-area contact surface. The large-area contact surface has a surface area greater than that of the small-area contact surface. The large-area contact surface and the small-area contact surface define therebetween an inclined angle that is not equal to 180 degrees. As such, efficacies that no wire is exposed, storage is easy, the outside appearance is neat and aesthetic, application is available for both large and small areas, no material will be wasted, excellent maneuverability may be achieved, and the use is easy are provided.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
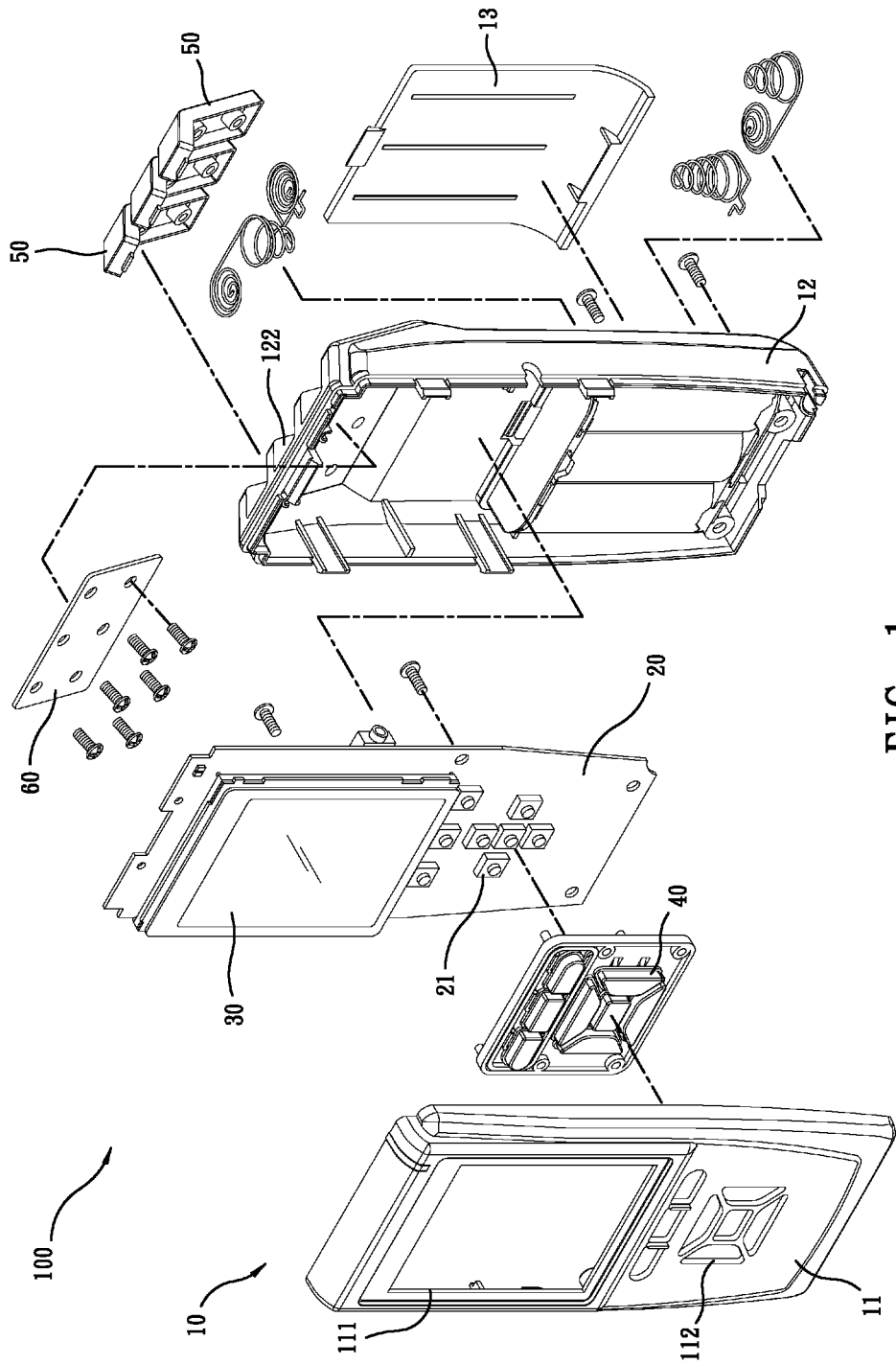
FIG. 1 is an exploded view of a preferred embodiment of the present invention.
Figure 2:
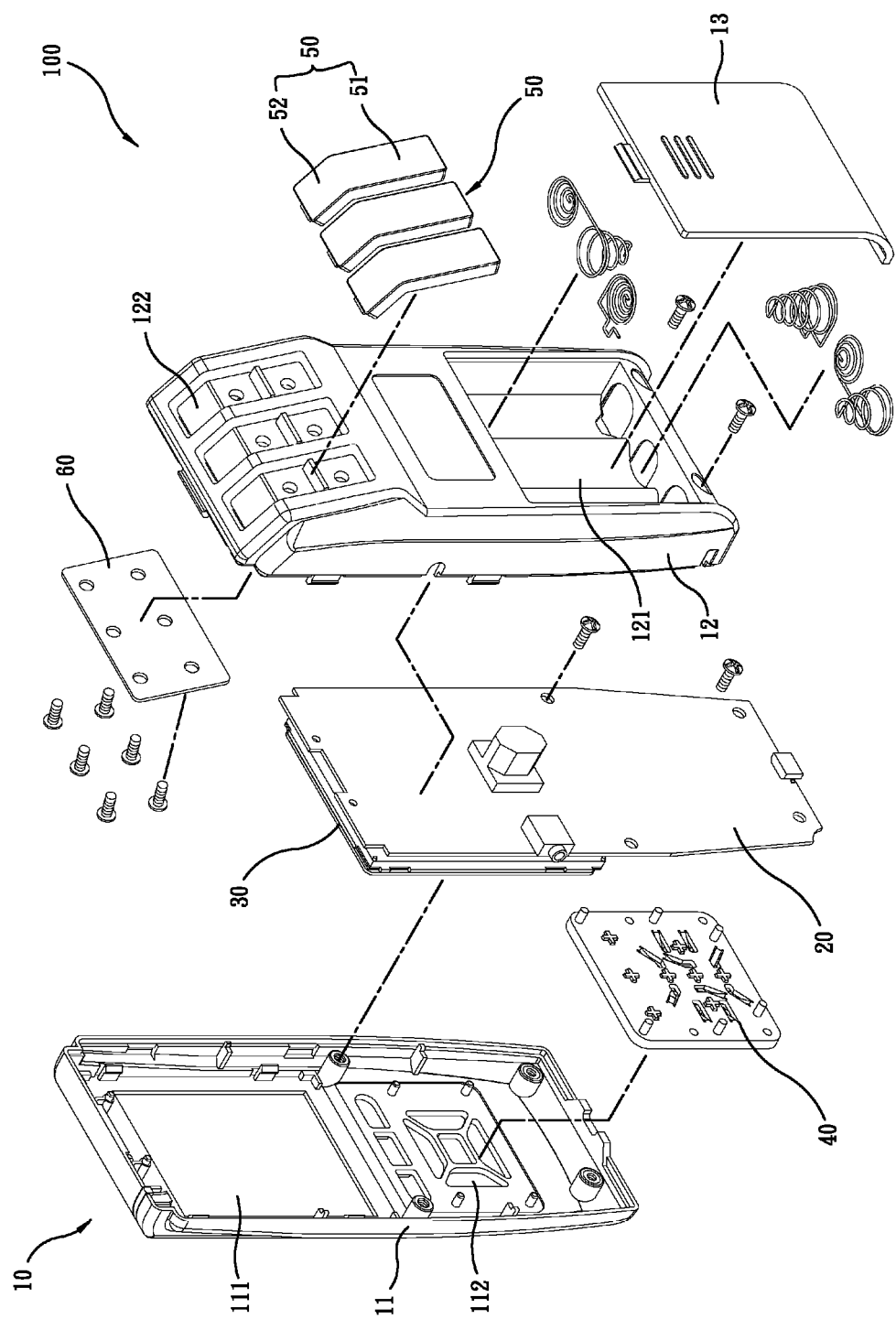
FIG. 2 is an exploded view of the embodiment shown in FIG. 1 but taken from a different perspective.
Figure 3:
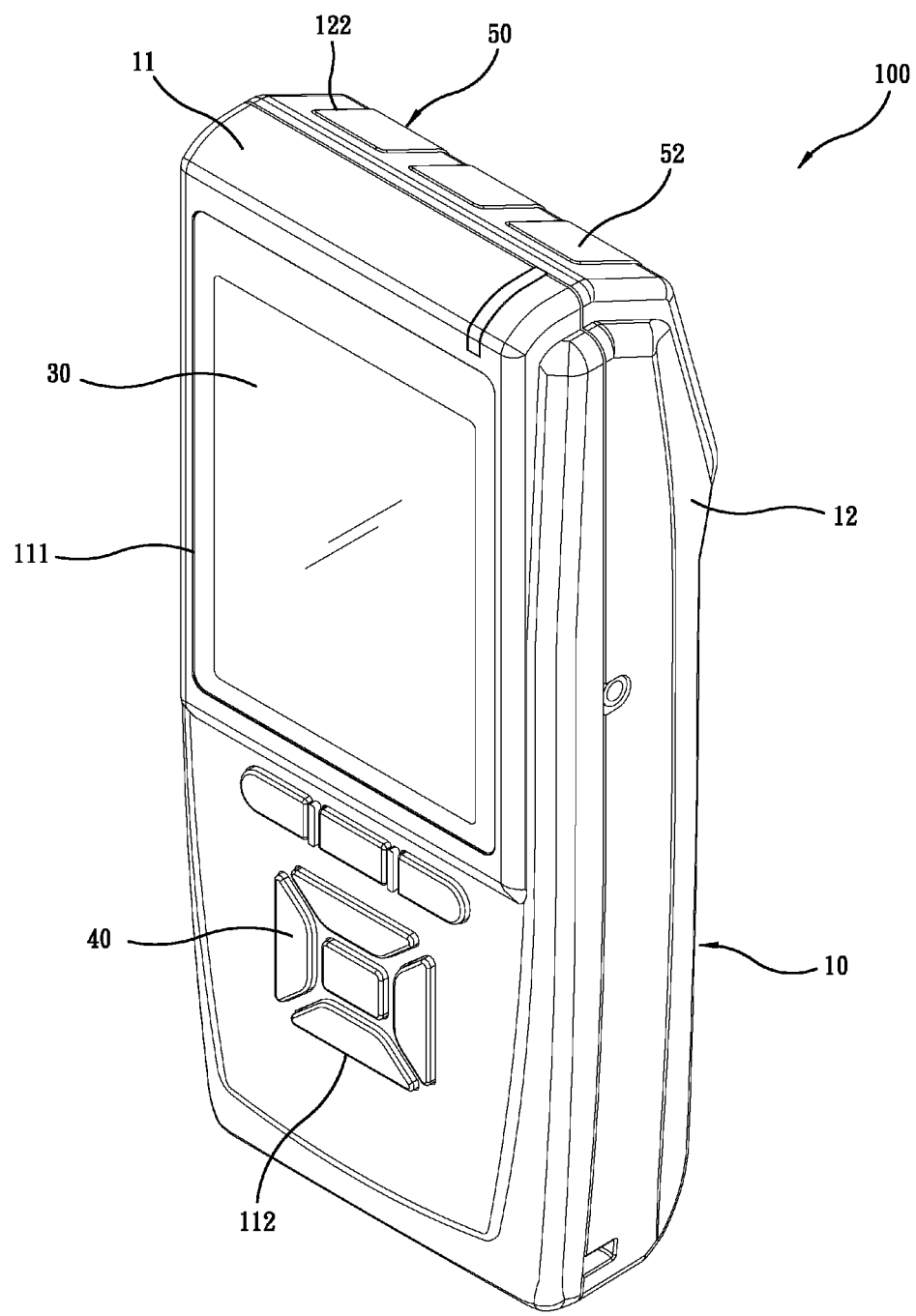
FIG. 3 is a perspective view of the embodiment of FIG. 1 in an assembled form.
Figure 4:
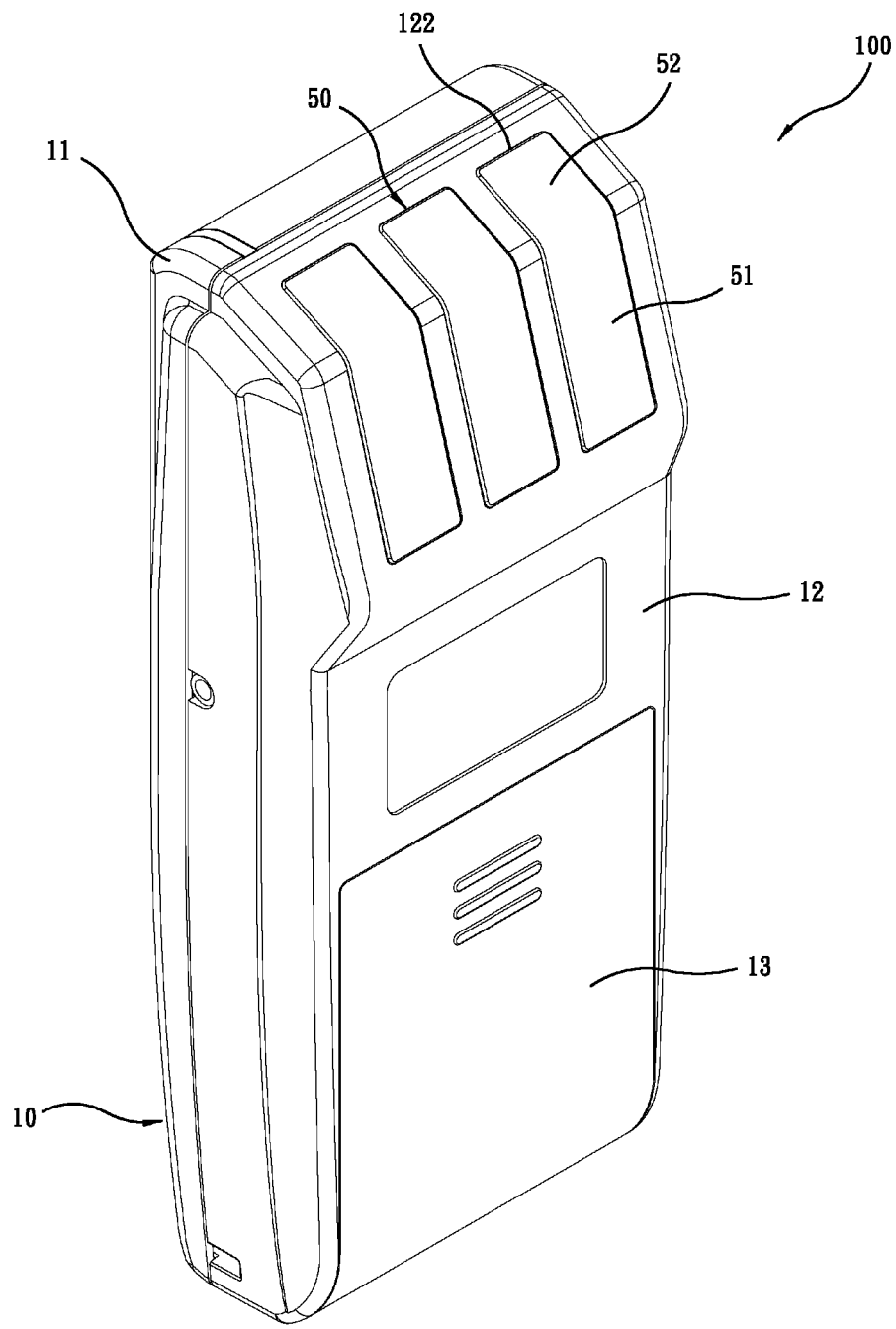
FIG. 4 is a perspective view of the embodiment of FIG. 1, but taken from a different perspective, in an assembled form.
Figure 5:
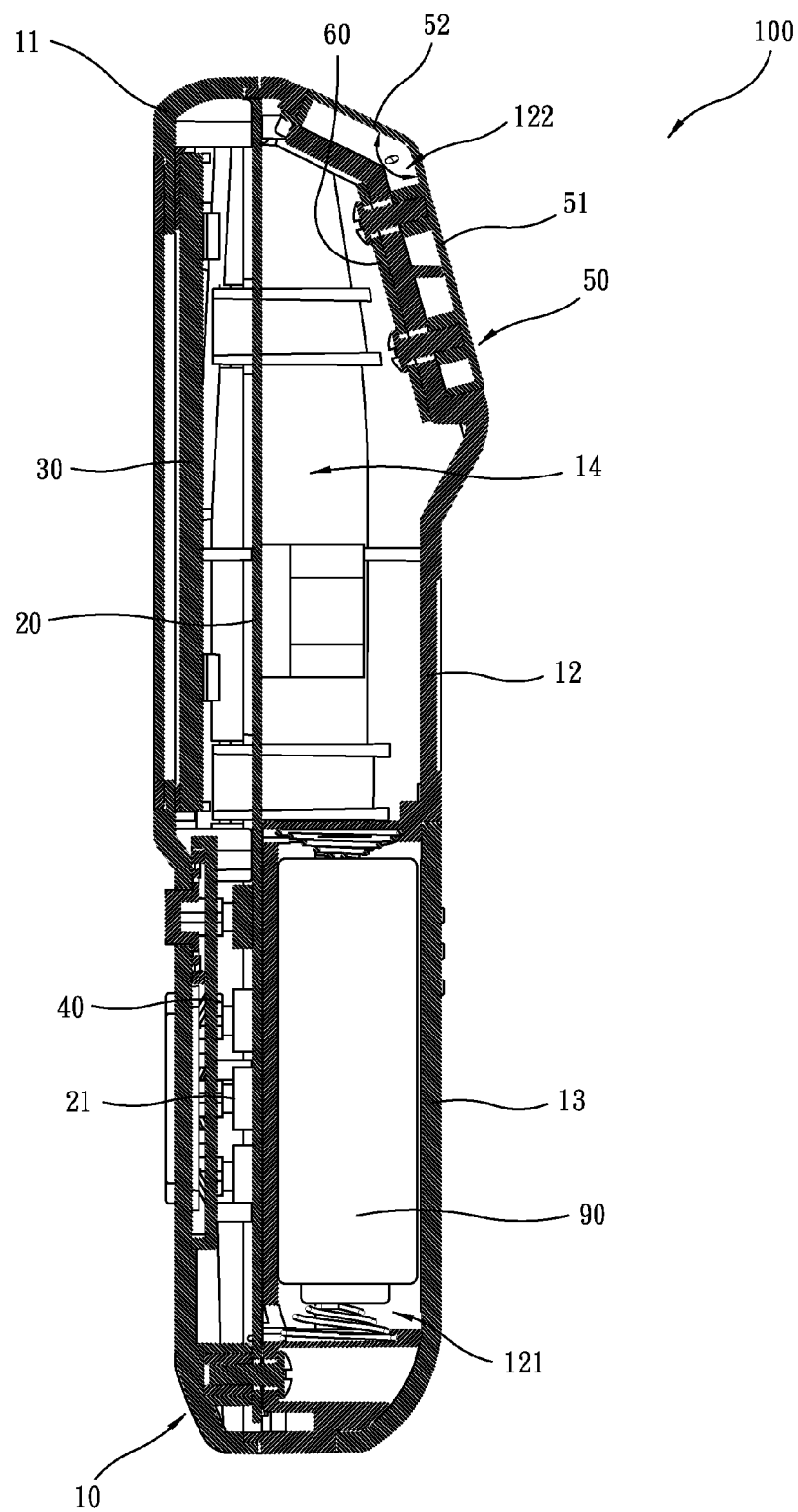
FIG. 5 is a cross-sectional view of the embodiment of FIG. 1.
Figure 6:
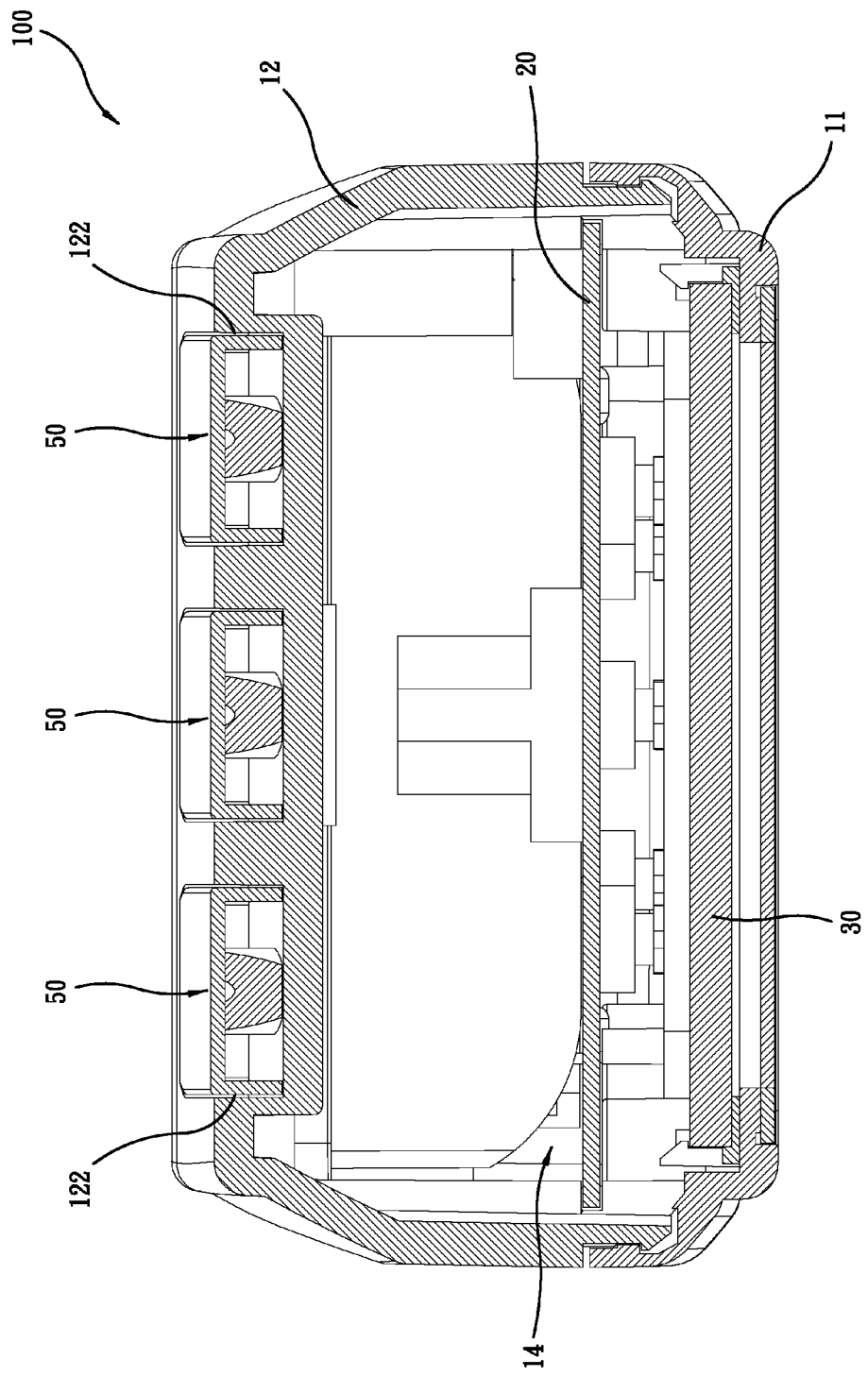
FIG. 6 is a cross-sectional view of the embodiment of FIG. 1.

Referring to FIGS. 1-6, a preferred embodiment of the present invention provides an electric stimulator 100, which generally comprises a housing 10, a control circuit board 20, a display screen 30, a pushbutton cover 40, a plurality of electrode plates 50, and a transmission interface circuit board 60.

Referring to FIGS. 1-6, the housing 10 comprises a front casing member 11, a rear casing member 12, and a battery lid 13. The front casing member 11 mates and is coupled to the rear casing member 12 so that an internal space 14 is defined between the front casing member 11 and the rear casing member 12. The front casing member 11 comprises a display screen opening 111 formed therein and communicating between the internal space 14 and the outside. The front casing member 11 comprises a plurality of pushbutton openings 112 formed therein and communicating between the internal space 14 and the outside. The rear casing member 12 has a back surface in which a battery compartment 121 and a plurality of electrode plate retention slots

122 that is spaced from each other by a predetermined interval are formed. The battery compartment 121 receives and holds a plurality of rechargeable batteries 90 therein. The battery lid 13 is attached, in a removable manner, to the rear casing member 12 to close the battery compartment 121.

Referring to FIGS. 1-6, the control circuit board 20 is fixedly mounted in the internal space 14 of the housing 10 to receive electrical power from the rechargeable batteries 90 for controlling intensity and frequency of a current output. The control circuit board 20 is provided thereon with a plurality of pushbuttons 21 to serve as an interface through which the control circuit board 20 can be controlled from the outside.

Referring to FIGS. 1-6, the display screen 30 is electrically connected to the control circuit board 20 and is received and retained in the display screen opening 111 of the housing 10 to be viewed by a user and for displaying a therapeutic project, frequency characteristics, output energy intensity, and a timer.

Referring to FIGS. 1-6, the pushbutton cover 40 is retained in the pushbutton openings 112 of the housing 10 and is set in contact engagement the pushbuttons 21 of the control circuit board 20 in order to reduce the potential risk of damage of the pushbuttons 21 and thus extend the life span of the pushbuttons 21.

Referring to FIGS. 1-6, the electrode plates 50 are generally stiff or rigid and are made of an electrically conductive material (such as an electrically conductive metal) and are respectively received and retained in the electrode plate retention slots 122 of the housing 10 in an outwards-protruding manner Each of the electrode plates 50 has an outer surface that comprises a large-area contact surface 51 and a small-area contact surface 52 connected to the large-area contact surface 51. The large-area contact surface 51 has a surface area greater than that of the small-area contact surface 52. Further, the large-area contact surface 51 and the small-area contact surface 52 define therebetween an included angle θ that is not equal to 180 degrees.

Referring to FIGS. 1-6, the transmission interface circuit board 60 is fixedly mounted in the internal space 14 of the housing 10 and is in electric connection with the control circuit board 20 and the electrode plates 50 in order to allow an electric current to be transmitted through the control circuit board and the transmission interface circuit board 60 to the electrode plates 50.

The components and assembly of the electric stimulator 100 according to a preferred embodiment of the present invention have been described above and, in the following, the operation thereof will be described.

To use the present invention, a user may contact the pushbutton cover 40 to press down one of the pushbuttons 21 for activating the present invention and controlling an output mode thereof, so that electric power supplied from the rechargeable batteries 90 is transmitted through the control circuit board 20 and the transmission interface circuit board 60 to the electrode plates 50.

This arrangement allows for better maneuverability and the user may move the present invention as desired to suit different needs so that the electrode plates 50 can be moved, through sliding, to various parts of a human body. Further, the large-area contact surfaces 51 can be used to provide electric stimulation to sites of the surface of the human body that have a large area, such as limbs and torso, or alternatively, the small-area contact surfaces 52 can be used to provide electric stimulation to sites of the surface of the human body that have a small area, such as a periphery of an eye, a corner of a mouth, and a forehead, whereby the convenience and accuracy of use are improved.

Further, although three electrode plates and three electrode plate retention slots are shown in the embodiment described above, with the electrode plates respectively received and retained in the electrode plate retention slots, in an actual application, the housing may comprise only one electrode plate retention slot and at least two electrode plates receivable in the electrode plate retention slot to achieve a similar effect.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. An electric stimulator, comprising:
a housing, which comprises an internal space formed therein and an outside surface in which at least one electrode plate retention slot is formed;
a control circuit board, which is mounted in the internal space of the housing to control intensity and frequency of a current output;
at least two electrode plates, which are electrically conductive and are received and retained in the electrode plate retention slot of the housing and are in electric connection with the control circuit board, the electrode plates having an outside surface that comprises a large-area contact surface and a small-area contact surface connected to the large-area contact surface, the large-area contact surface having a surface area that is greater than a surface area of the small-area contact surface, the large-area contact surface and the small-area contact surface defining therebetween an included angle that is not equal to 180 degrees;
wherein the electrode plates each comprises a first flat section and a second flat section that are connected to each other at a predetermined angle therebetween and wherein the first flat section comprises the large-area contact surface and the second flat section comprises the small-area contact surface, the predetermined angle between the first and second flat section being the included angle defined between the large-area contact surface and the small-area contact surface.

2. The electric stimulator according to claim 1, wherein the housing comprise a front casing member, a rear casing member, and a battery lid, the front casing member being combinable with the rear casing member in such a way that the internal space is defined between the front casing member and the rear casing member, the rear casing member comprising a battery compartment and the electrode plate retention slot formed therein, the battery compartment adapted to receive and retain therein a rechargeable battery, the battery lid being removably coupled to the rear casing member to close the battery compartment.

3. The electric stimulator according to claim 2 further comprising a display screen, the front casing member comprising a display screen opening formed therein and adapted to communicate between the internal space and the outside, the display screen being electrically connected to the control circuit board and received and retained in the display screen opening of the front casing member for being viewed by a user.

4. The electric stimulator according to claim 2 further comprising a pushbutton cover, the front casing member comprising a plurality of pushbutton openings formed therein and adapted to communicate between the internal space and the outside, the control circuit board comprising a plurality of pushbuttons provided thereon to serve as an interface for allowing the control circuit board to be controlled from the outside, the pushbutton cover being received and retained in the pushbutton openings of the front casing member and in engagement with the pushbuttons of the control circuit board.

5. The electric stimulator according to claim 1 further comprising a transmission interface circuit board mounted in the internal space of the housing and in electric connection with the control circuit board and the electrode plates to allow an electric current to be transmitted through the control circuit board and the transmission interface circuit board to the electrode plates.

6. The electric stimulator according to claim 1 further comprising a display screen, the housing comprising a display screen opening formed therein and adapted to communicate between the internal space and the outside, the display screen being electrically connected to the control circuit board and received and retained in the display screen opening of the housing for being viewed by a user.

7. The electric stimulator according to claim 1 further comprising a pushbutton cover, the housing comprising a plurality of pushbutton openings formed therein and adapted to communicate between the internal space and the outside, the control circuit board comprising a plurality of pushbuttons provided thereon to serve as an interface for allowing the control circuit board to be controlled from the outside, the pushbutton cover being received and retained in the pushbutton openings of the housing and in engagement with the pushbuttons of the control circuit board.

8. The electric stimulator according to claim 1 comprising three electrode plates, the housing comprising three electrode plate retention slots formed in the outside surface, the electrode plates being respectively received and retained in the electrode plate retention slots.

\* \* \* \* \*